US012121658B2

(12) United States Patent
Mahon et al.

(10) Patent No.: US 12,121,658 B2
(45) Date of Patent: Oct. 22, 2024

(54) TRACHEOSTOMY DILATOR (71) Applicant: TELEFLEX LIFE SCIENCES UNLIMITED COMPANY, Athlone (IE)

(72) Inventors: Adrian Mahon, Walshisland (IE); Joanne Fayne, Athlone (IE); Cathal Tighe, Athlone (IE); Gavin Reynolds, Cloone (IE); Katy Ryan, Monkstown (IE)

(73) Assignee: TELEFLEX LIFE SCIENCES UNLIMITED COMPANY, Athlone (IE)

( * ) Notice: Subject to any disclaimer, the term of this patent is extended or adjusted under 35 U.S.C. 154(b) by 353 days.

(21) Appl. No.: 17/525,940

(22) Filed: Nov. 14, 2021

(65) Prior Publication Data
US 2022/0088335 A1 Mar. 24, 2022

Related U.S. Application Data (63) Continuation of application No. PCT/IB2020/054638, filed on May 15, 2020.

(60) Provisional application No. 62/848,310, filed on May 15, 2019.

(51) Int. Cl.
*A61M 16/04* (2006.01)
(52) U.S. Cl.
CPC .... *A61M 16/0472* (2013.01); *A61M 16/0475* (2014.02)

(58) Field of Classification Search
CPC .. A61M 16/00; A61M 16/0003; A61M 16/04; A61M 16/0465; A61M 16/0468; A61M 16/047; A61M 16/0472
See application file for complete search history.

(56) References Cited

U.S. PATENT DOCUMENTS

| 672,377 | A | 4/1901 | Kearns |
| 2,564,118 | A | 8/1951 | Mahorner |
| 3,443,564 | A | 5/1969 | Heinz |
| 3,511,243 | A | 5/1970 | Toy |
| 3,754,554 | A | 8/1973 | Felbarg |
| 3,893,454 | A | 7/1975 | Hagelin |
| 3,908,637 | A | 9/1975 | Doroshow |
| 3,908,665 | A | 9/1975 | Moses |
| 3,916,903 | A | 11/1975 | Pozzi |

(Continued)

FOREIGN PATENT DOCUMENTS

| CN | 104797285 A | 7/2015 |
| EP | 1099451 A2 | 5/2001 |

(Continued)

*Primary Examiner* — Colin W Stuart
(74) *Attorney, Agent, or Firm* — BakerHostetler (57) ABSTRACT A tracheostomy dilator may include a distal portion, a handle portion, a lumen, and a proximal portion. The distal portion may have a curve extending to a distal opening and be configured to dilate a tracheostomy. The handle portion may be proximal of the distal portion and be configured to be grasped by a user. The lumen may be configured to receive a guidewire. The proximal portion may be proximal of the handle portion and have a proximal opening in communication with the lumen. The proximal portion may be configured to deflect the guidewire at an angle of at least 30 degrees from a longitudinal axis of the handle portion.

18 Claims, 6 Drawing Sheets (56) References Cited

U.S. PATENT DOCUMENTS

| | | |
|---|---|---|
| 3,957,055 A | 5/1976 | Linder et al. |
| 4,054,135 A | 10/1977 | Berman |
| 4,067,331 A | 1/1978 | Berman |
| 4,068,658 A | 1/1978 | Berman |
| 4,069,820 A | 1/1978 | Berman |
| 4,100,246 A | 7/1978 | Frisch |
| 4,211,234 A | 7/1980 | Fisher |
| 4,338,930 A | 7/1982 | Williams |
| 4,364,391 A | 12/1982 | Toye |
| 4,405,314 A | 9/1983 | Cope |
| 4,449,522 A | 5/1984 | Baum |
| 4,454,887 A | 6/1984 | Krueger |
| 4,471,778 A | 9/1984 | Toye |
| 4,512,765 A | 4/1985 | Muto |
| 4,531,933 A | 7/1985 | Norton et al. |
| 4,762,128 A | 8/1988 | Rosenbluth |
| 4,771,776 A | 9/1988 | Powell et al. |
| 4,820,270 A | 4/1989 | Hardcastle et al. |
| 4,832,020 A | 5/1989 | Augustine |
| 4,893,623 A | 1/1990 | Rosenbluth |
| 4,898,163 A | 2/1990 | George |
| 4,966,583 A | 10/1990 | Debbas |
| 4,978,334 A | 12/1990 | Toye et al. |
| 5,021,043 A | 6/1991 | Becker et al. |
| 5,034,005 A | 7/1991 | Appling |
| 5,042,469 A | 8/1991 | Augustine |
| 5,058,580 A | 10/1991 | Hazard |
| 5,143,093 A | 9/1992 | Sahota |
| RE34,086 E | 10/1992 | George |
| 5,169,386 A | 12/1992 | Becker et al. |
| 5,183,463 A | 2/1993 | Debbas |
| 5,183,464 A | 2/1993 | Dubrul et al. |
| 5,186,168 A | 2/1993 | Spofford et al. |
| 5,188,100 A | 2/1993 | Miles et al. |
| 5,197,465 A | 3/1993 | Montgomery |
| 5,209,725 A | 5/1993 | Roth |
| 5,209,735 A | 5/1993 | Lazarus |
| 5,217,005 A | 6/1993 | Weinstein |
| 5,217,007 A | 6/1993 | Ciaglia |
| 5,222,487 A | 6/1993 | Carr et al. |
| 5,246,421 A | 9/1993 | Saab |
| 5,259,371 A | 11/1993 | Tonrey |
| 5,263,931 A | 11/1993 | Miller |
| 5,275,611 A | 1/1994 | Behl |
| 5,279,280 A | 1/1994 | Bacich et al. |
| 5,279,285 A | 1/1994 | Griggs |
| 5,297,546 A | 3/1994 | Spofford et al. |
| 5,300,023 A | 4/1994 | Lowery et al. |
| 5,312,360 A | 5/1994 | Behl |
| 5,338,296 A | 8/1994 | Dalessandro et al. |
| 5,364,345 A | 11/1994 | Lowery et al. |
| 5,374,247 A | 12/1994 | Lowery et al. |
| 5,382,238 A | 1/1995 | Abrahamson et al. |
| 5,389,074 A | 2/1995 | Parker et al. |
| 5,395,335 A | 3/1995 | Jang |
| 5,484,409 A | 1/1996 | Atkinson et al. |
| 5,515,844 A | 5/1996 | Christopher |
| 5,549,553 A | 8/1996 | Ressemann et al. |
| 5,623,924 A | 4/1997 | Lindenman et al. |
| 5,653,230 A | 8/1997 | Ciaglia et al. |
| 5,669,380 A | 9/1997 | Garry et al. |
| 5,697,365 A | 12/1997 | Pell |
| 5,718,683 A | 2/1998 | Ressemann et al. |
| 5,749,357 A | 5/1998 | Linder |
| 5,752,932 A | 5/1998 | Ellis et al. |
| 5,891,057 A | 4/1999 | Chaisson et al. |
| 5,904,648 A | 5/1999 | Arndt et al. |
| 5,921,971 A | 7/1999 | Agro et al. |
| 5,980,484 A | 11/1999 | Ressemann et al. |
| 6,007,522 A | 12/1999 | Agro et al. |
| 6,010,520 A | 1/2000 | Pattison |
| 6,086,548 A | 7/2000 | Chaisson et al. |
| 6,096,009 A | 8/2000 | Windheuser et al. |
| 6,152,910 A | 11/2000 | Agro et al. |
| 6,270,465 B1 | 8/2001 | Keith et al. |
| 6,299,628 B1 | 10/2001 | Harrison et al. |
| 6,312,404 B1 | 11/2001 | Agro et al. |
| 6,346,093 B1 | 2/2002 | Allman et al. |
| 6,443,912 B1 | 9/2002 | Mazzola et al. |
| 6,494,887 B1 | 12/2002 | Kaladelfos |
| 6,520,951 B1 | 2/2003 | Carrillo et al. |
| 6,530,898 B1 | 3/2003 | Nimkar et al. |
| 6,582,401 B1 | 6/2003 | Windheuser et al. |
| 6,606,515 B1 | 8/2003 | Windheuser et al. |
| 6,637,435 B2 | 10/2003 | Ciaglia et al. |
| 6,638,253 B2 | 10/2003 | Breznock |
| 6,663,597 B1 | 12/2003 | Windheuser et al. |
| D485,358 S | 1/2004 | Woo |
| 6,705,320 B1 | 3/2004 | Anderson |
| 6,742,519 B2 | 6/2004 | Turnbull |
| 6,746,442 B2 | 6/2004 | Agro et al. |
| 6,792,948 B2 | 9/2004 | Brain |
| 6,869,416 B2 | 3/2005 | Windheuser et al. |
| 6,879,854 B2 | 4/2005 | Windheuser et al. |
| 6,924,348 B2 | 8/2005 | Tajiri et al. |
| 6,997,908 B2 | 2/2006 | Carrillo et al. |
| 7,036,510 B2 | 5/2006 | Zgoda et al. |
| 7,060,052 B2 | 6/2006 | Windheuser et al. |
| 7,076,285 B2 | 7/2006 | Windheuser et al. |
| 7,089,942 B1 | 8/2006 | Grey |
| 7,179,252 B2 | 2/2007 | Agro et al. |
| 7,267,124 B1 | 9/2007 | Roberson et al. |
| 7,305,989 B2 | 12/2007 | Gostelow |
| 7,316,708 B2 | 1/2008 | Gordon et al. |
| 7,326,197 B2 | 2/2008 | Breznock et al. |
| 7,331,966 B2 | 2/2008 | Soma et al. |
| 7,341,061 B2 | 3/2008 | Wood |
| 7,373,939 B1 | 5/2008 | Dubois et al. |
| 7,544,193 B2 | 6/2009 | Agro et al. |
| 7,600,515 B2 | 10/2009 | Matlock |
| D605,759 S | 12/2009 | Cuevas et al. |
| 7,631,642 B2 | 12/2009 | Freitag et al. |
| 7,647,929 B2 | 1/2010 | Matlock et al. |
| 7,650,886 B1 | 1/2010 | Keller et al. |
| 7,670,316 B2 | 3/2010 | Windheuser et al. |
| 7,695,467 B2 | 4/2010 | Breznock et al. |
| 7,706,861 B2 | 4/2010 | Windheuser et al. |
| 7,708,744 B2 | 5/2010 | Soma et al. |
| 7,811,303 B2 | 10/2010 | Fallin et al. |
| 7,846,133 B2 | 12/2010 | Windheuser et al. |
| 7,909,811 B2 | 3/2011 | Agro et al. |
| 7,921,847 B2 | 4/2011 | Totz |
| 7,975,696 B2 | 7/2011 | Blom |
| 7,985,213 B2 | 7/2011 | Parker |
| 8,043,208 B2 | 10/2011 | Windheuser et al. |
| 8,075,608 B2 | 12/2011 | Gordon et al. |
| 8,146,598 B2 | 4/2012 | Matlock et al. |
| 8,151,791 B2 | 4/2012 | Arlow et al. |
| 8,182,529 B2 | 5/2012 | Gordon et al. |
| 8,186,350 B2 | 5/2012 | Matlock |
| 8,186,353 B1 | 5/2012 | Lejeune |
| 8,202,289 B2 | 6/2012 | Woo |
| 8,206,283 B2 | 6/2012 | Windheuser et al. |
| 8,307,824 B2 | 11/2012 | Cuevas et al. |
| 8,313,687 B2 | 11/2012 | Sleva et al. |
| 8,343,105 B2 | 1/2013 | Windheuser et al. |
| 8,372,107 B2 | 2/2013 | Tupper |
| 8,424,534 B2 | 4/2013 | Lyons et al. |
| 8,474,450 B2 | 7/2013 | Diaz Jimenez |
| 8,474,459 B2 | 7/2013 | Schnell |
| 8,561,605 B2 | 10/2013 | Davis |
| 8,568,436 B2 | 10/2013 | Ciaglia et al. |
| 8,579,881 B2 | 11/2013 | Agro et al. |
| 8,607,795 B2 | 12/2013 | Cuevas et al. |
| 8,709,064 B2 | 4/2014 | Rasmussen et al. |
| 8,721,720 B2 | 5/2014 | Margolin et al. |
| 8,757,161 B2 | 6/2014 | Guerra |
| 8,820,319 B2 | 9/2014 | Schwartz et al. |
| 8,845,525 B2 | 9/2014 | Mcgrath et al. |
| 8,876,848 B2 | 11/2014 | Stien et al. |
| 8,887,717 B2 | 11/2014 | Levitan |
| 8,899,225 B2 | 12/2014 | Bosel |
| 8,985,099 B2 | 3/2015 | Freitag et al. |
| 8,997,745 B2 | 4/2015 | Matlock |

(56) References Cited

U.S. PATENT DOCUMENTS

| | | |
|---|---|---|
| 8,997,746 B2 | 4/2015 | Matlock et al. |
| 8,997,748 B2 | 4/2015 | Margolin et al. |
| 9,089,663 B2 | 7/2015 | Rosenbaum et al. |
| 9,155,856 B2 | 10/2015 | Munaro |
| 9,162,033 B2 | 10/2015 | Enk |
| 9,211,385 B2 | 12/2015 | Schnell |
| 9,226,651 B2 | 1/2016 | Mcgrath et al. |
| 9,265,907 B2 | 2/2016 | Hoffa |
| 9,320,596 B2 | 4/2016 | Margolin et al. |
| 9,387,009 B2 | 7/2016 | Fatone et al. |
| 9,393,374 B2 | 7/2016 | Levitan |
| 9,414,743 B2 | 8/2016 | Mcgrath |
| 9,555,206 B1 | 1/2017 | Raimondi et al. |
| 9,572,623 B2 | 2/2017 | Long |
| 9,662,001 B2 | 5/2017 | Mcgrath et al. |
| 9,675,772 B2 | 6/2017 | Brain |
| 9,693,890 B2 | 7/2017 | Kochem et al. |
| 9,700,312 B2 | 7/2017 | Kostrzewski et al. |
| 9,737,290 B2 | 8/2017 | Fatone et al. |
| 9,770,194 B2 | 9/2017 | Azagury et al. |
| 9,855,396 B2 | 1/2018 | Topping et al. |
| 9,931,494 B2 | 4/2018 | Rasulo et al. |
| 9,949,629 B2 | 4/2018 | Gardner |
| 9,974,533 B2 | 5/2018 | Fatone et al. |
| 10,058,668 B2 | 8/2018 | Wondka et al. |
| 10,065,009 B2 | 9/2018 | Bonutti |
| 10,071,215 B2 | 9/2018 | Bonutti |
| 10,166,353 B2 | 1/2019 | Pecherer |
| 10,194,791 B2 | 2/2019 | Mcgrath et al. |
| 10,194,895 B2 | 2/2019 | Fatone et al. |
| 10,758,695 B2 | 9/2020 | Krimsky et al. |
| 11,020,555 B2 | 6/2021 | Jeffrey et al. |
| 2002/0026149 A1 | 2/2002 | Agro et al. |
| 2002/0066453 A1 | 6/2002 | Ciaglia et al. |
| 2003/0018309 A1 | 1/2003 | Breznock |
| 2003/0045892 A1 | 3/2003 | Kaladelfos |
| 2003/0050407 A1 | 3/2003 | Tajiri et al. |
| 2003/0088153 A1 | 5/2003 | Carrillo et al. |
| 2003/0114871 A1 | 6/2003 | Turnbull |
| 2003/0136414 A1 | 7/2003 | Turnbull |
| 2003/0199826 A1 | 10/2003 | Windheuser et al. |
| 2003/0233043 A1 | 12/2003 | Windheuser et al. |
| 2004/0035432 A1 | 2/2004 | Gostelow |
| 2004/0087905 A1 | 5/2004 | Breznock et al. |
| 2004/0087991 A1 | 5/2004 | Woo |
| 2004/0098013 A1 | 5/2004 | Ciaglia et al. |
| 2004/0106852 A1 | 6/2004 | Windheuser et al. |
| 2004/0111095 A1 | 6/2004 | Gordon et al. |
| 2004/0139971 A1 | 7/2004 | Brain |
| 2004/0154623 A1 | 8/2004 | Schaeffer et al. |
| 2004/0167439 A1* | 8/2004 | Sharrow ............... A61M 25/09 600/585 |
| 2004/0193142 A1 | 9/2004 | Agro et al. |
| 2004/0236346 A1 | 11/2004 | Parker |
| 2004/0255951 A1 | 12/2004 | Grey |
| 2004/0255954 A1 | 12/2004 | Zgoda et al. |
| 2005/0080443 A1 | 4/2005 | Fallin et al. |
| 2005/0103345 A1 | 5/2005 | Brain |
| 2005/0119673 A1 | 6/2005 | Gordon et al. |
| 2005/0148950 A1 | 7/2005 | Windheuser et al. |
| 2005/0177043 A1 | 8/2005 | Windheuser et al. |
| 2005/0197663 A1 | 9/2005 | Soma et al. |
| 2006/0004398 A1 | 1/2006 | Binder et al. |
| 2006/0100657 A2 | 5/2006 | Ciaglia et al. |
| 2006/0124134 A1 | 6/2006 | Wood |
| 2006/0206097 A1 | 9/2006 | Breznock et al. |
| 2006/0229496 A1 | 10/2006 | Windheuser et al. |
| 2006/0247523 A1 | 11/2006 | Windheuser et al. |
| 2007/0017527 A1 | 1/2007 | Totz |
| 2007/0068531 A1 | 3/2007 | Matlock et al. |
| 2007/0083262 A1 | 4/2007 | Matlock |
| 2007/0149948 A1 | 6/2007 | Agro et al. |
| 2008/0029088 A1 | 2/2008 | Freitag |
| 2008/0109059 A1 | 5/2008 | Gordon et al. |
| 2008/0114374 A1 | 5/2008 | Soma et al. |
| 2008/0275391 A1 | 11/2008 | Lyons et al. |
| 2009/0013787 A1 | 1/2009 | Esnouf |
| 2009/0024089 A1 | 1/2009 | Levine et al. |
| 2009/0090357 A1 | 4/2009 | Schwartz et al. |
| 2009/0090365 A1 | 4/2009 | Cuevas et al. |
| 2009/0090366 A1 | 4/2009 | Cuevas et al. |
| 2009/0091066 A1 | 4/2009 | Sleva et al. |
| 2009/0159087 A1 | 6/2009 | Isla |
| 2009/0163942 A1 | 6/2009 | Cuevas et al. |
| 2009/0178674 A1 | 7/2009 | Schnell |
| 2009/0194102 A1 | 8/2009 | Chen et al. |
| 2009/0199849 A1 | 8/2009 | Enk |
| 2009/0209908 A1 | 8/2009 | Cuevas et al. |
| 2009/0227985 A1 | 9/2009 | Agro et al. |
| 2009/0259309 A1 | 10/2009 | Blom |
| 2009/0306472 A1 | 12/2009 | Filipi et al. |
| 2009/0312784 A1 | 12/2009 | Tupper |
| 2009/0320833 A1 | 12/2009 | Cuevas et al. |
| 2009/0320834 A1 | 12/2009 | Cuevas et al. |
| 2009/0320854 A1 | 12/2009 | Cuevas et al. |
| 2010/0012130 A1 | 1/2010 | Guerra |
| 2010/0037898 A1 | 2/2010 | Matlock |
| 2010/0043786 A1 | 2/2010 | Freitag et al. |
| 2010/0065062 A1 | 3/2010 | Rajan et al. |
| 2010/0078031 A1 | 4/2010 | Matlock et al. |
| 2010/0083957 A1 | 4/2010 | Davis |
| 2010/0114147 A1 | 5/2010 | Biyani |
| 2010/0160726 A1 | 6/2010 | Windheuser et al. |
| 2010/0163050 A1 | 7/2010 | Hoffa |
| 2010/0174139 A1 | 7/2010 | Windheuser et al. |
| 2010/0191183 A1 | 7/2010 | Tanghoej et al. |
| 2010/0224187 A1 | 9/2010 | Dalton |
| 2010/0256451 A1 | 10/2010 | Mcgrath et al. |
| 2010/0275911 A1 | 11/2010 | Arlow et al. |
| 2010/0300448 A1 | 12/2010 | Kenowski et al. |
| 2010/0300449 A1 | 12/2010 | Chan et al. |
| 2010/0300451 A1 | 12/2010 | Griffith et al. |
| 2010/0312059 A1 | 12/2010 | Mcgrath |
| 2011/0060315 A1 | 3/2011 | Windheuser et al. |
| 2011/0196344 A1 | 8/2011 | Agro et al. |
| 2011/0208226 A1 | 8/2011 | Fatone et al. |
| 2011/0265797 A1 | 11/2011 | Waldron |
| 2011/0290245 A1 | 12/2011 | Cuevas et al. |
| 2012/0017913 A1 | 1/2012 | Schumacher et al. |
| 2012/0017916 A1 | 1/2012 | Schumacher et al. |
| 2012/0095295 A1 | 4/2012 | Mcgrath et al. |
| 2012/0095432 A1 | 4/2012 | Nath |
| 2012/0123464 A1 | 5/2012 | Rasmussen et al. |
| 2012/0138064 A1 | 6/2012 | Margolin et al. |
| 2012/0145147 A1 | 6/2012 | Freitag et al. |
| 2012/0160238 A1 | 6/2012 | Matlock et al. |
| 2012/0165936 A1 | 6/2012 | Margolin et al. |
| 2012/0180787 A1 | 7/2012 | Bosel |
| 2012/0199120 A1 | 8/2012 | Matlock |
| 2012/0204867 A1 | 8/2012 | Levitan |
| 2012/0298102 A1 | 11/2012 | Levitan |
| 2013/0025588 A1 | 1/2013 | Bosel |
| 2013/0255694 A1 | 10/2013 | Arlow et al. |
| 2013/0261393 A1 | 10/2013 | Munaro |
| 2013/0269689 A1 | 10/2013 | Brain |
| 2013/0269705 A1 | 10/2013 | Kochem et al. |
| 2013/0317439 A1 | 11/2013 | Ellingwood et al. |
| 2013/0331880 A1 | 12/2013 | Stien et al. |
| 2014/0000627 A1 | 1/2014 | Rosenbaum et al. |
| 2014/0020681 A1 | 1/2014 | Davis |
| 2014/0039492 A1 | 2/2014 | Long |
| 2014/0083432 A1 | 3/2014 | Servillo et al. |
| 2014/0121463 A1 | 5/2014 | Mcgrath et al. |
| 2014/0228679 A1 | 8/2014 | Bonutti |
| 2014/0228952 A1 | 8/2014 | Margolin et al. |
| 2014/0283821 A1 | 9/2014 | Levitan |
| 2015/0073343 A1 | 3/2015 | Nath |
| 2015/0080763 A1 | 3/2015 | Bonutti |
| 2015/0126908 A1 | 5/2015 | Azagury et al. |
| 2015/0151093 A1 | 6/2015 | Rasulo et al. |
| 2015/0209030 A1 | 7/2015 | Kostrzewski et al. |
| 2015/0250969 A1 | 9/2015 | Xavier et al. |

(56) References Cited

U.S. PATENT DOCUMENTS

| | | |
|---|---|---|
| 2015/0258296 A1 | 9/2015 | Pecherer |
| 2016/0015557 A1 | 1/2016 | Kochem et al. |
| 2016/0015944 A1 | 1/2016 | Jenkins et al. |
| 2016/0081542 A1 | 3/2016 | Mcgrath et al. |
| 2016/0106940 A1 | 4/2016 | Bosel |
| 2016/0184543 A1 | 6/2016 | Topping et al. |
| 2016/0220772 A1 | 8/2016 | Krimsky et al. |
| 2016/0287827 A1 | 10/2016 | Bonutti |
| 2016/0310123 A1 | 10/2016 | Fatone et al. |
| 2016/0338581 A1 | 11/2016 | Mcgrath |
| 2017/0196445 A1 | 7/2017 | Gardner |
| 2017/0251916 A1 | 9/2017 | Mcgrath et al. |
| 2017/0274193 A1 | 9/2017 | Nath |
| 2017/0281156 A1 | 10/2017 | Kostrzewski et al. |
| 2017/0340317 A1 | 11/2017 | Fatone et al. |
| 2017/0360597 A1 | 12/2017 | Kochem et al. |
| 2018/0008308 A1 | 1/2018 | Ellingwood et al. |
| 2018/0008793 A1 | 1/2018 | Brain |
| 2018/0085031 A1 | 3/2018 | Azagury et al. |
| 2018/0169364 A1 | 6/2018 | Jeffrey et al. |
| 2018/0207383 A1 | 7/2018 | Gardner |
| 2018/0242833 A1 | 8/2018 | Gardner |
| 2018/0242963 A1 | 8/2018 | Fatone et al. |
| 2018/0280647 A1 * | 10/2018 | Schnell ............ A61M 16/0497 |
| 2020/0324068 A1 | 10/2020 | Chambers |

FOREIGN PATENT DOCUMENTS

| | | | |
|---|---|---|---|
| EP | 3025749 A1 * | 6/2016 | ........ A61M 16/0472 |
| GB | 2365352 A | 2/2002 | |
| JP | 2004-148122 A | 5/2004 | |
| JP | 2005-095401 A | 4/2005 | |
| JP | 2009-544344 A | 12/2009 | |
| JP | 2017-164423 A | 9/2017 | |
| JP | 2018-518316 A | 7/2018 | |
| WO | 2006/008602 A2 | 1/2006 | |
| WO | 2006/087032 A1 | 8/2006 | |
| WO | 2006/087512 A1 | 8/2006 | |
| WO | 2008/009943 A1 | 1/2008 | |
| WO | 2008/015094 A1 | 2/2008 | |
| WO | 2008/113985 A1 | 9/2008 | |
| WO | 2011/012677 A1 | 2/2011 | |
| WO | 2011/024013 A1 | 3/2011 | |
| WO | 2011/103629 A1 | 9/2011 | |
| WO | 2014/019014 A1 | 2/2014 | |
| WO | 2015/078114 A1 | 6/2015 | |
| WO | 2016/158475 A1 | 10/2016 | |

* cited by examiner

TRACHEOSTOMY DILATOR

PRIORITY

The present application is a continuation of International Application No. PCT/IB2020/054638, filed on May 15, 2020, which claims the benefit of priority to U.S. Provisional Patent Application No. 62/848,310, filed on May 15, 2019, the disclosures of which are expressly incorporated herein by reference in their entirety.

TECHNICAL FIELD

The present disclosure relates generally to dilators, and more particularly to percutaneous tracheostomy dilators configured to reduce or prevent pinching of a guidewire.

BACKGROUND

Percutaneous tracheostomies can be formed by inserting a hollow needle through the skin into the trachea and inserting a guidewire along the needle in the opening. The needle is then withdrawn, and a tracheostomy dilator is passed over the guidewire to expand the opening for the insertion of a tracheostomy tube. The present invention solves one or more problems involving the tracheostomy dilators of the prior art.

OVERVIEW

One aspect of the present invention is directed to a tracheostomy dilator including a distal portion, a handle portion, a lumen, and a proximal portion. The distal portion may have a curve extending to a distal opening and be configured to dilate a tracheostomy. As used herein, the term "tracheostomy" may refer to the surgical formation of an opening into the trachea through the neck, or may refer to the opening itself, as commonly understood in the art. The handle portion may be proximal of the distal portion and be configured to be grasped by a user. The lumen may be configured to receive a guidewire. The proximal portion may be proximal of the handle portion and have a proximal opening in communication with the lumen. The proximal portion may be configured to deflect the guidewire at an angle of at least 30 degrees from a longitudinal axis of the handle portion.

In some embodiments, the angle may be at least 45 degrees from the longitudinal axis of the handle portion. In some embodiments, the handle portion may be substantially straight. In some embodiments, the handle portion may be textured. In some embodiments, the handle portion may include a textured sleeve. In some embodiments, the distal portion may have a wall thickness that decreases along a length of the distal portion. In some embodiments, the tracheostomy dilator may further include an indicator of a size of the tracheostomy dilator on the distal portion. In some embodiments, the proximal opening may be disposed at the angle from the longitudinal axis. In some embodiments, the proximal portion may have a bend extending from the longitudinal axis to the angle from the longitudinal axis. In some embodiments, the proximal portion may be longitudinally aligned with the longitudinal axis of the handle portion. In some embodiments, the proximal portion may have a bevel in a circumferential wall at the proximal opening, such that the circumferential wall extends further proximally at an upper portion than a lower portion. In some embodiments, the bevel may be curved. In some embodiments, the proximal portion may have a hole distal of the proximal opening and in communication with the proximal opening, and the hole is configured to receive the guidewire. In some embodiments, the proximal portion may have a slot connecting the proximal opening and the hole, and the slot may have a width less than the proximal opening and the hole. In some embodiments, the proximal portion may be rotatable around the longitudinal axis relative to the handle portion. In some embodiments, the proximal portion may be detachable from the handle portion. In some embodiments, the proximal portion may include an insert having a tubular segment received within the handle portion to detachably secure the proximal portion to the handle portion.

Another aspect of the present invention is directed to a tracheostomy dilator including a distal portion, a handle portion, a lumen, and a proximal portion. The distal portion may have a curve extending to a distal opening and be configured to dilate a tracheostomy. The handle portion may be proximal of the distal portion and be configured to be grasped by a user. The lumen may be configured to receive a guidewire. The proximal portion may be proximal of the handle portion and have a proximal opening in communication with the lumen. The proximal portion may have a bevel.

In some embodiments, the bevel may be in a circumferential wall at the proximal opening, such that the circumferential wall extends further proximally at an upper portion than a lower portion. In some embodiments, the proximal portion may be longitudinally aligned with the longitudinal axis of the handle portion. In some embodiments, the proximal portion further may include a hole distal of the proximal opening and in communication with the proximal opening, and the hole is configured to receive the guidewire. In some embodiments, the proximal portion may include a slot connecting the proximal opening and the hole, and the slot may have a width less than the proximal opening and the hole.

BRIEF DESCRIPTION OF THE DRAWINGS

In order that the invention may be readily understood, aspects of this invention are illustrated by way of examples in the accompanying drawings.

The same reference numbers may be used in the drawings and the following detailed description to refer to the same or similar parts.

DETAILED DESCRIPTION

Figure 1A:
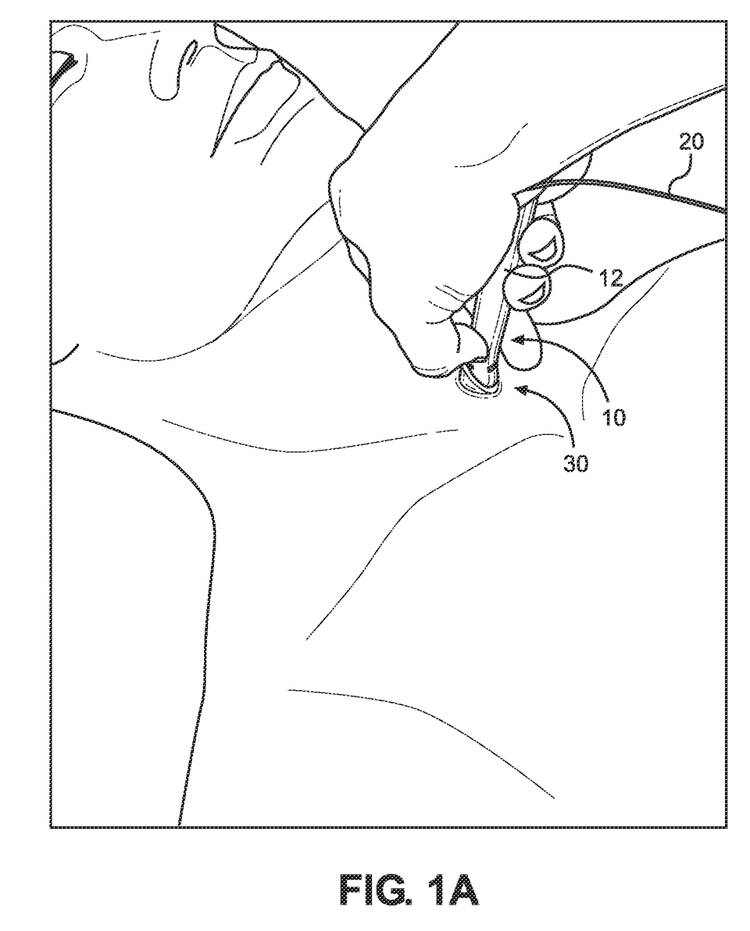
FIGS. 1A-1B illustrate a percutaneous insertion of a tracheostomy dilator into a tracheostomy.
Figure 1B:
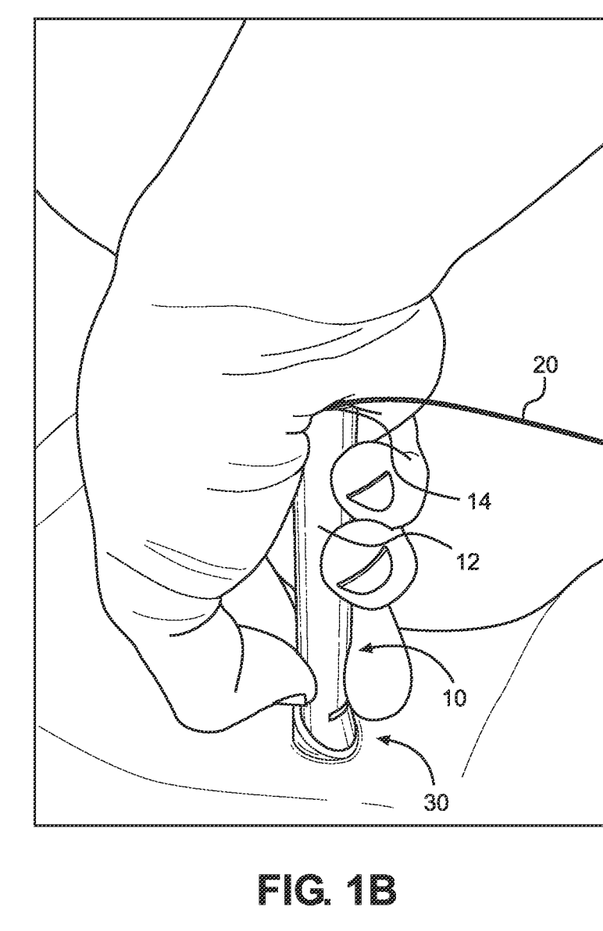

FIGS. 1A-1B illustrate a tracheostomy dilator 10 inserted over a guidewire 20 into a tracheostomy 30. A distal end (not shown) of the tracheostomy dilator 10 is configured to dilate the tracheostomy 30 for insertion of a tracheostomy tube (not shown). A handle portion 12 of the tracheostomy dilator 10 is grasped by a user as the tracheostomy dilator 10 is inserted over the guidewire 20 into the tracheostomy 30. As the tracheostomy dilator 10 is advanced over the guidewire 20, the guidewire 20 exits through a proximal opening 14 at the proximal end of the handle portion 12. The proximal opening 14 is disposed along the longitudinal axis of the handle portion 12, such that as the user pushes the tracheostomy dilator 10 into the tracheostomy 30, the user's palm tends to cover the proximal opening 14 and/or to pinch the guidewire 20 against the proximal end of the handle portion 12. This accidental pinching of the guidewire 20 may cause a number of complications including the undesirable pushing the guidewire 20 further into the trachea as the tracheostomy dilator 10 is advanced and/or pulling the guidewire 20 out of the trachea as the tracheostomy dilator 10 is removed. The present disclosure is directed to mitigating and/or overcoming one or more of these problems, and/or other problems associated with tracheostomy dilators and/or dilators in general.

The present disclosure is directed to tracheostomy dilators configured to shield and/or deflect the guidewire away from the longitudinal axis of the handle portion to reduce or prevent interference from the hand of the user. In some embodiments, the tracheostomy dilators may deflect the guidewire at least 30 degrees from the longitudinal axis of the handle portion, while the handle portion is substantially straight to facilitate grasping. In some embodiments, the tracheostomy dilators may deflect the guidewire at least 45 degrees from the longitudinal axis of the handle portion. The deflection of the guidewire may be caused by a bend at a proximal portion the tracheostomy dilator between the handle portion and a proximal opening. The bend may include a sharp bevel and/or a curve. In some embodiments, the proximal portion may be beveled at a face of the proximal opening, such that a circumferential wall of the proximal portion extends further proximally at an upper portion than a lower portion, effectively shielding the guidewire when grasped from above. In some embodiments, the proximal portion may, additionally or alternatively, include a hole through the bottom of the bottom portion and in communication with the proximal opening. The hole may connect to the proximal opening with a narrow slot, such that the guidewire may be received in the hole to reduce or prevent the chance of pinching when the user grasps the handle from above. In some embodiments, the proximal portion may be rotatable around the longitudinal axis of the handle portion and/or detachable from the handle portion. Thus, the various embodiments of the tracheostomy dilator may shield and/or deflect the guidewire to reduce or prevent pinching of the guidewire by the hand of the user against the proximal end of the tracheostomy dilator.

Figures 2A, 2B, 2C:
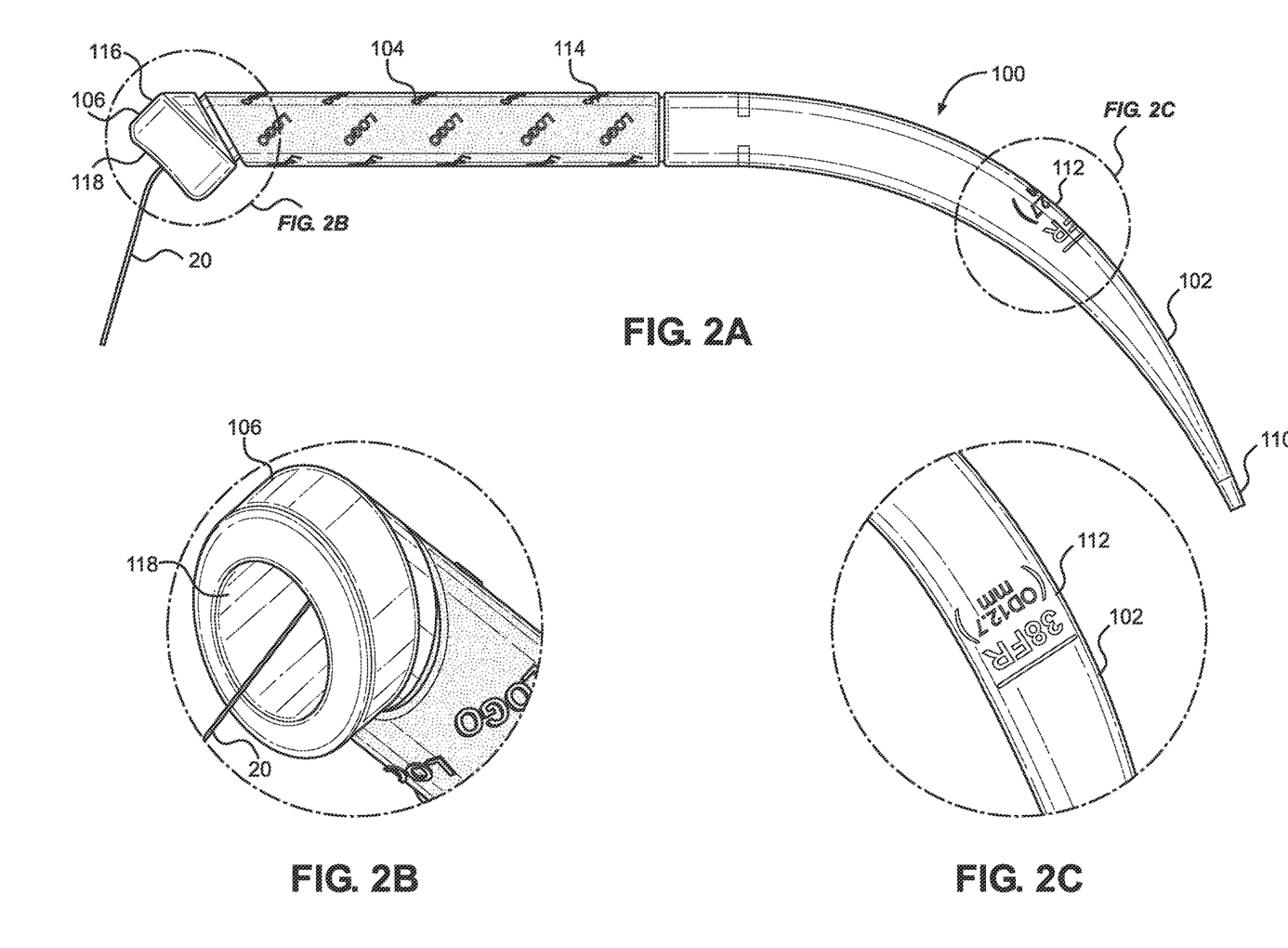
FIGS. 2A-2C illustrate a first exemplary embodiment of a tracheostomy dilator according to the present invention.

FIGS. 2A-2C illustrate a first exemplary embodiment of a tracheostomy dilator 100. The tracheostomy dilator 100 may include a distal portion 102, a handle portion 104, a proximal portion 106, and a lumen extending therethrough.

The distal portion 102 may including a continuous curve extending from the handle portion 104 to a distal tip 110 having a distal opening of the lumen. The continuous curve may enable the tracheostomy dilator 100 to pass through the trachea during insertion and for the distal tip 110 to clear the posterior tracheal wall. The distal portion 102 may taper along the continuous curve to the distal tip 110 to facilitate insertion. For example, the distal portion 102 may taper through a wall thickness that gradually reduces along the continuous curve to the distal tip 110. The distal portion 102 may have a hydrophilic coating to reduce friction during insertion into the tracheostomy, obviating the need for lubricating jelly. The distal portion 102 may also include indicia 112 of a size of a cross-section and a depth of the distal portion 102. For example, as illustrated in FIG. 2C, the indicia 112 may include a diameter (e.g., 38 French) and a line at least partially around the circumference indicating a proper depth for insertion of the distal portion 102 to dilate the tracheostomy.

The handle portion 104 may be substantially straight and include an elongated linear shaft integrally formed with the distal portion 102. The handle portion 104 may be proximal of the distal portion 102 and be configured to be grasped by a user. The handle portion 104 may be textured to increase grip and handling of the user. For example, the handle portion 104 may include a textured rubber sleeve 114 over the shaft. The grip on the textured surface may be enhanced by embossing a plurality of raised words and/or logos (e.g., of the manufacturer and/or distributor) along the length of the handle portion 104 and/or sleeve 114. The sleeve 114 may be received in an elongate recess on the outer surface of the shaft to prevent relative slipping.

The proximal portion 106 may be configured to deflect a guidewire 20 at an angle of least 30-45 degrees from a longitudinal axis of the handle portion 104. The proximal portion 106 may be integral to the elongated linear shaft of the handle portion 104 and/or the distal portion 102. The proximal portion 106 may include a bevel 116 that disposes a longitudinal axis of a proximal opening 118 of the proximal portion 106 at the angle of at least 30-45 degrees from the longitudinal axis of the handle portion 104. The deflected guidewire 20 may pass out of the proximal opening 118 of the tracheostomy dilator 100 when advanced. The proximal portion 106 may have a round cross-section with an outer surface and a lumen having a longitudinal axis disposed at the angle of least 30-45 degrees from a longitudinal axis of the handle portion 104. Due to the relative angle of the proximal portion 106 and proximal opening 118, pinching of the guidewire 20 by fingers and/or palms is reduced or prevented w % ben the user grasps the handle portion 104.

Figures 3A, 3B, 3C:
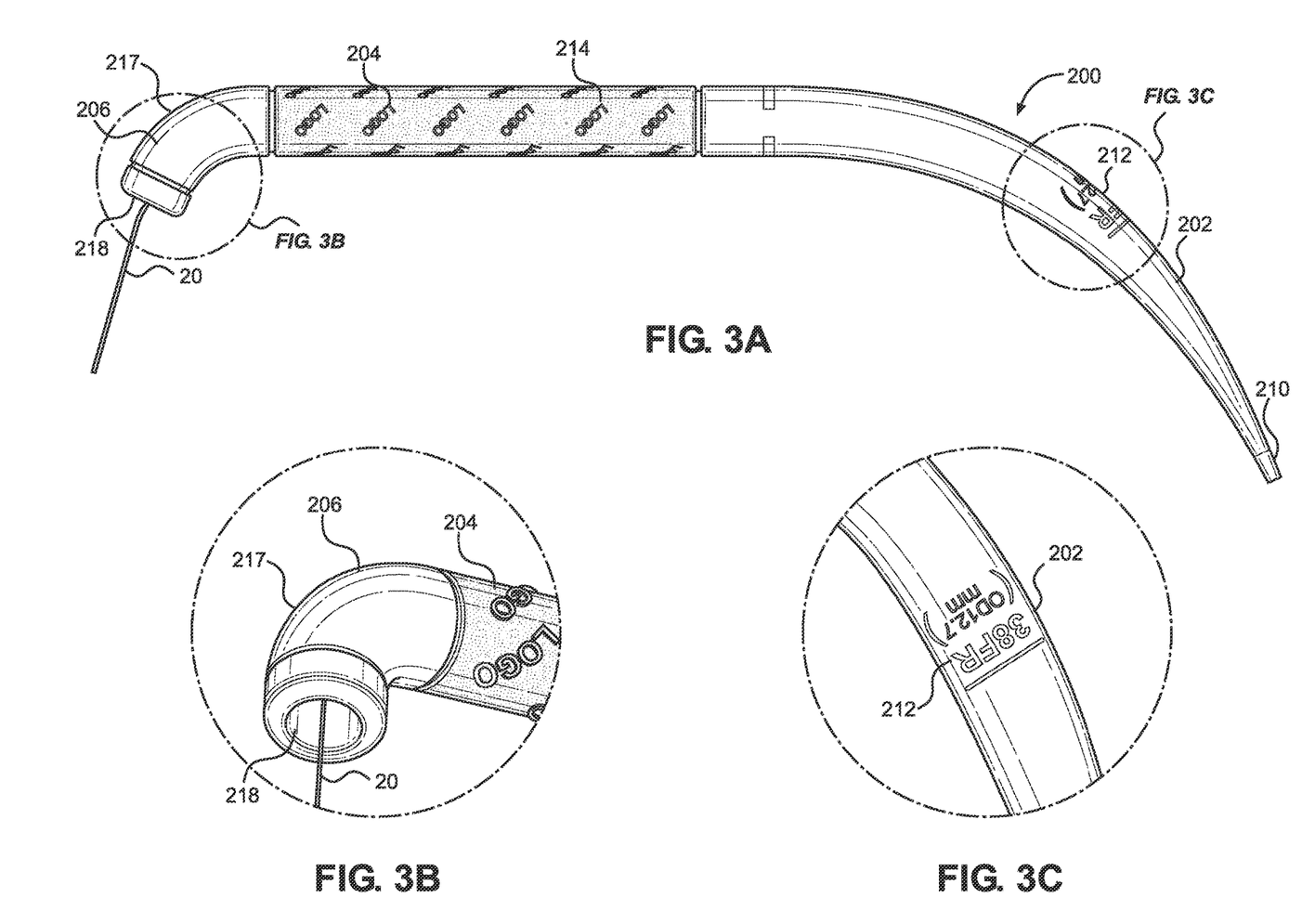
FIGS. 3A-3C illustrate a second exemplary embodiment of a tracheostomy dilator according to the present invention.

FIGS. 3A-3C illustrate a second exemplary embodiment of a tracheostomy dilator 200. The tracheostomy dilator 200 may include a distal portion 202, a handle portion 204, a proximal portion 206, and a lumen extending therethrough.

The distal portion 202 may including a continuous curve extending from the handle portion 204 to a distal tip 210 having a distal opening of the lumen. The continuous curve may enable the tracheostomy dilator 200 to pass through the trachea during insertion and for the distal tip 210 to clear the posterior tracheal wall. The distal portion 202 may taper along the continuous curve to the distal tip 210 to facilitate insertion. For example, the distal portion 202 may taper through a wall thickness that gradually reduces along the continuous curve to the distal tip 210. The distal portion 202 may have a hydrophilic coating to reduce friction during insertion into the tracheostomy, obviating the need for lubricating jelly. The distal portion 202 may also include indicia 212 of a size of a cross-section and depth of the distal portion 202. For example, as illustrated in FIG. 3C, the indicia 212 may include a diameter (e.g., 38 French) and a line at least partially around the circumference indicating a proper depth for insertion of the distal portion 202 to dilate the tracheostomy.

The handle portion 204 may be substantially straight and include an elongated linear shaft integrally formed with the distal portion 202. The handle portion 204 may be proximal of the distal portion 202 and be configured to be grasped by a user. The handle portion 204 may be textured to increase grip and handling of the user. For example, the handle portion 204 may include a textured rubber sleeve 214 over the shaft. The grip on the textured surface may be enhanced by embossing a plurality of raised words and/or logos (e.g., of the manufacturer and/or distributor) along the length of the handle portion 204 and/or sleeve 214. The sleeve 214 may be received in an elongate recess on the outer surface of the shaft to prevent relative slipping.

The proximal portion 206 may be configured to deflect a guidewire 20 at an angle of least 30-45 degrees from a longitudinal axis of the handle portion 204. The proximal portion 206 may be integral to the elongated linear shaft of the handle portion 204 and/or the distal portion 202. The proximal portion 206 may include a curve 217 that disposes a longitudinal axis of a proximal opening 218 at the angle of at least 30-45 degrees from the longitudinal axis of the handle portion 204. The deflected guidewire 20 may passes out of the proximal opening 218 of the tracheostomy dilator 200 when advanced. The proximal portion 206 may have a round cross-section with an outer surface curving to the angle of least 30-45 degrees from a longitudinal axis of the handle portion 204. Due to the relative angle of the proximal portion 206 and proximal opening 218, pinching of the guidewire 20 by fingers and/or palms is reduced or prevented when the user grasps the handle portion 204.

Figure 4A:
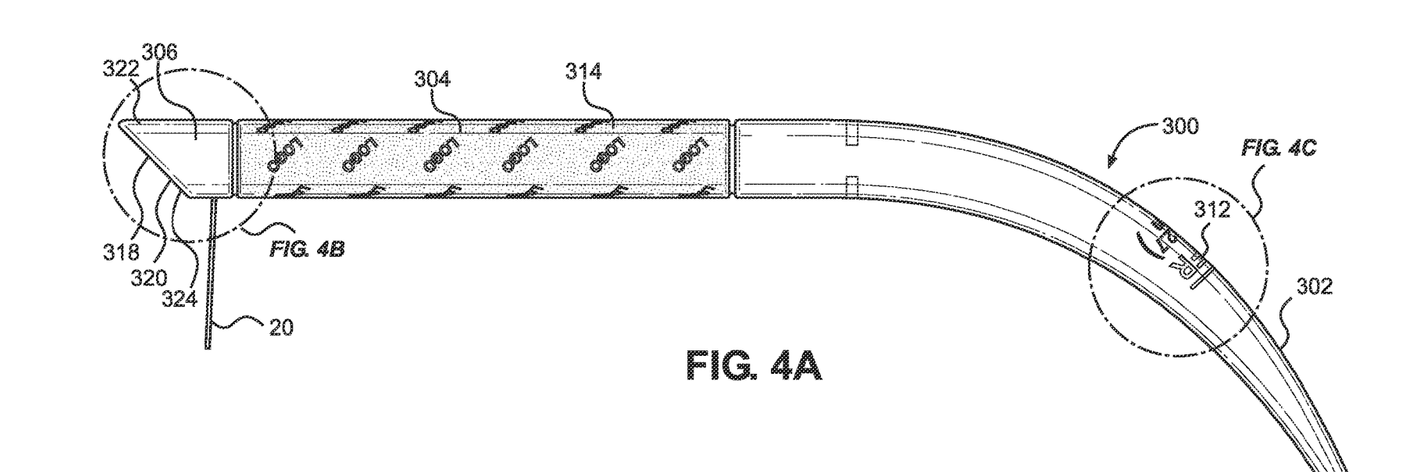
FIGS. 4A-4C illustrate a third exemplary embodiment of a tracheostomy dilator according to the present invention.
Figure 4B:
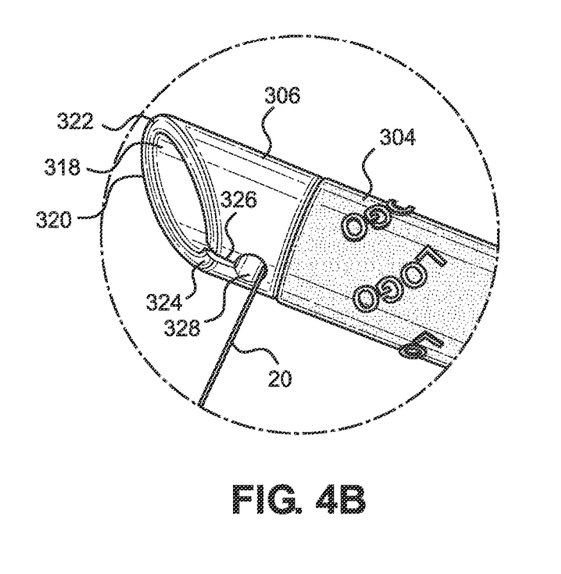
Figure 4C:
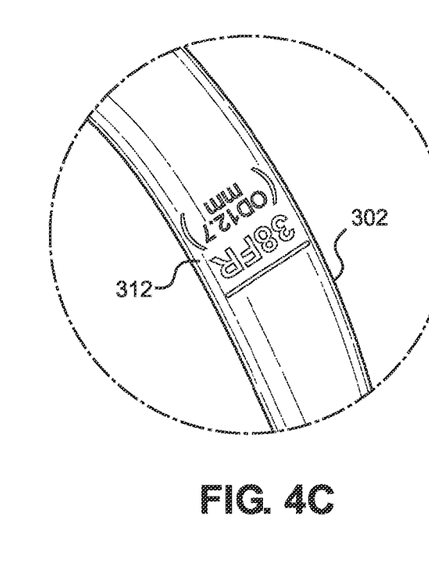

FIGS. 4A-4C illustrate a third exemplary embodiment of a tracheostomy dilator 300. The tracheostomy dilator 300 may include a distal portion 302, a handle portion 304, a proximal portion 306, and a lumen extending therethrough.

The distal portion 302 may including a continuous curve extending from the handle portion 304 to a distal tip 310 having a distal opening of the lumen. The continuous curve may enable the tracheostomy dilator 300 to pass through the trachea during insertion and for the distal tip 310 to clear the posterior tracheal wall. The distal portion 302 may taper along the continuous curve to the distal tip 310 to facilitate insertion. For example, the distal portion 302 may taper through a wall thickness that gradually reduces along the continuous curve to the distal tip 310. The distal portion 302 may have a hydrophilic coating to reduce friction during insertion into the tracheostomy, obviating the need for lubricating jelly. The distal portion 302 may also include indicia 312 of a size of a cross-section and depth of the distal portion 302. For example, as illustrated in FIG. 4C, the indicia 312 may include a diameter (e.g., 38 French) and a line at least partially around the circumference indicating a proper depth for insertion of the distal portion 302 to dilate tracheostomy.

The handle portion 304 may be substantially straight and include an elongated linear shaft integrally formed with the distal portion 302. The handle portion 304 may be proximal of the distal portion 302 and be configured to be grasped by a user. The handle portion 304 may be textured to increase grip and handling of the user. For example, the handle portion 304 may include a textured rubber sleeve 314 over the shaft. The grip on the textured surface may be enhanced by embossing a plurality of raised words and/or logos (e.g., of the manufacturer and/or distributor) along the length of the handle portion 304 and/or sleeve 314. The sleeve 314 may be received in an elongate recess on the outer surface of the shaft to prevent relative slipping.

The proximal portion 306 may be configured to deflect a guidewire 20 at an angle of least 30-45 degrees from a longitudinal axis of the handle portion 304. The proximal portion 306 may be integral to the elongated linear shaft of the handle portion 304 and/or the distal portion 302. The proximal portion 306 may include a proximal opening 318 of the lumen, through which the deflected guidewire 20 may pass out of the tracheostomy dilator 300 when advanced.

The proximal opening 318 may include a bevel 320, such that the circumferential wall of the proximal portion 306 extends further proximally at an upper portion 322 than a lower portion 324, effectively shielding the guidewire 20 when grasped from above. The proximal portion 306 may be longitudinally aligned with the longitudinal axis of the handle portion 304, and the bevel 320 may be disposed at about 45 degrees from the longitudinal axis. The lower portion 324 may have a slot 326 and a hole 328, both distal of the proximal opening 318 and in communication with the proximal opening 318 and the lumen. The slot 326 may be narrower than the proximal opening 318 and/or the hole 328. The guidewire 20 may be deflected downward from the proximal opening 318 through the hole 328 and into the slot 326 to reduce or prevent pinching when grasping the handle portion 304 from above.

Figures 5A, 5B, 5C:
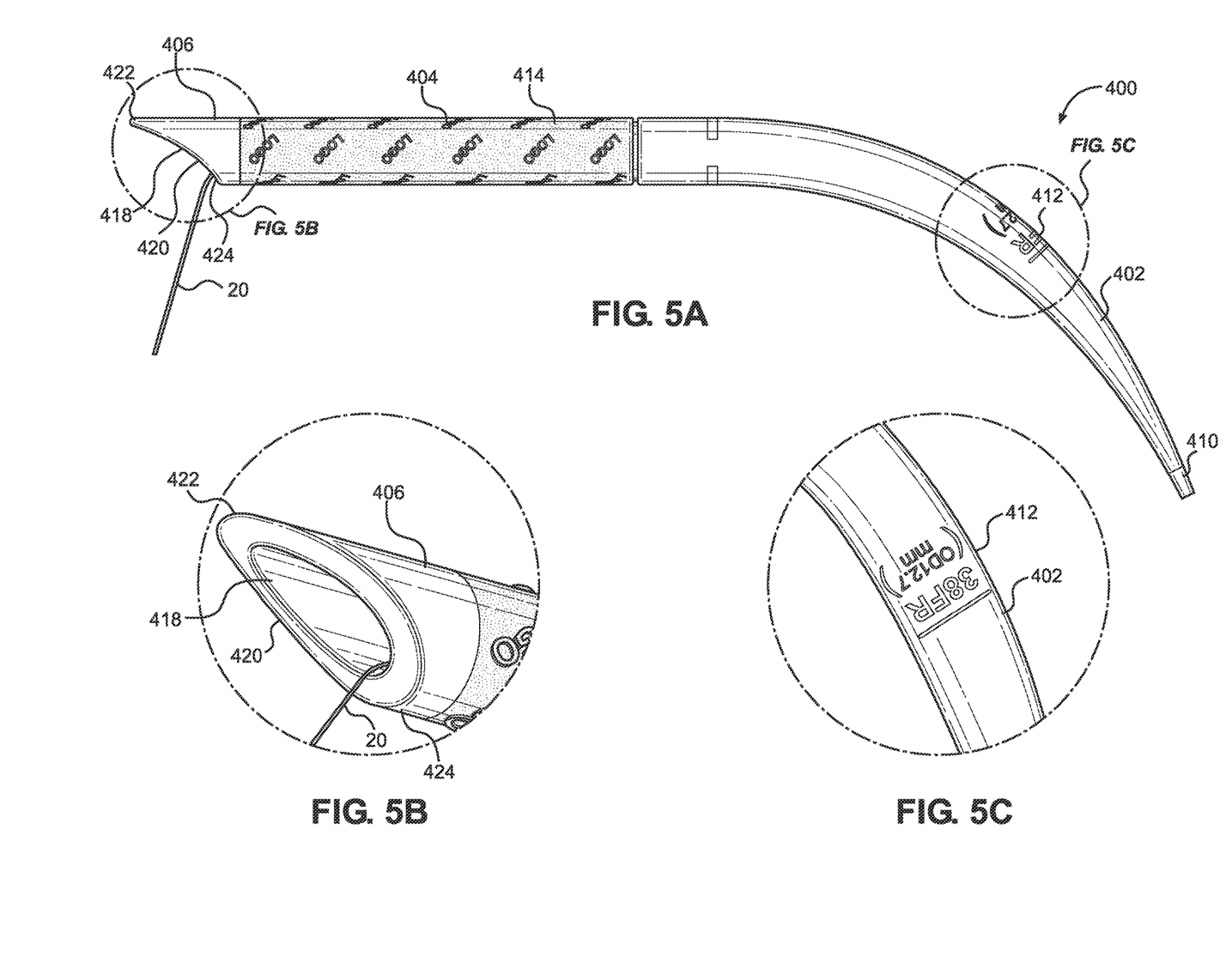
FIGS. 5A-5C illustrate a fourth exemplary embodiment of a tracheostomy dilator according to the present invention.

FIGS. 5A-5C illustrate a fourth exemplary embodiment of a tracheostomy dilator 400. The tracheostomy dilator 400 may include a distal portion 402, a handle portion 404, a proximal portion 406, and a lumen extending therethrough.

The distal portion 402 may including a continuous curve extending from the handle portion 404 to a distal tip 410 having a distal opening of the lumen. The continuous curve may enable the tracheostomy dilator 400 to pass through the trachea during insertion and for the distal tip 410 to clear the posterior tracheal wall. The distal portion 402 may taper along the continuous curve to the distal tip 410 to facilitate insertion. For example, the distal portion 402 may taper through a wall thickness that gradually reduces along the continuous curve to the distal tip 410. The distal portion 402 may have a hydrophilic coating to reduce friction during insertion into the tracheostomy, obviating the need for lubricating jelly. The distal portion 402 may also include indicia 412 of a size of a cross-section and depth of the distal portion 402. For example, as illustrated in FIG. 5C, the indicia 412 may include a diameter (e.g., 38 French) and a line at least partially around the circumference indicating a proper depth for insertion of the distal portion 402 to dilate the tracheostomy.

The handle portion 404 may be substantially straight and include an elongated linear shaft integrally formed with the distal portion 402. The handle portion 404 may be proximal of the distal portion 402 and be configured to be grasped by a user. The handle portion 404 may be textured to increase grip and handling of the user. For example, the handle portion 404 may include a textured rubber sleeve 414 over the shaft. The grip on the textured surface may be enhanced by embossing a plurality of raised words and/or logos (e.g., of the manufacturer and/or distributor) along the length of the handle portion 404 and/or sleeve 414. The sleeve 414 may be received in an elongate recess on the outer surface of the shaft to prevent relative slipping.

The proximal portion 406 may be integral to the elongated linear shaft of the handle portion 404 and/or the distal portion 402. The proximal portion 406 may be longitudinally aligned with the longitudinal axis of the handle portion 404. The proximal portion 406 may include a proximal opening 418 of the lumen, through which the guidewire 20 may pass out of the tracheostomy dilator 400 when advanced. The proximal opening 418 may include a bevel 420, such that the circumferential wall of the proximal portion 406 extends further proximally at an upper portion 422 than a lower portion 424, effectively shielding the guidewire 20 when grasped from above. The bevel 420 may be curved.

FIGS. 6A-6D illustrate a fifth exemplary embodiment of a tracheostomy dilator 500. The tracheostomy dilator 500 may include a distal portion 502, a handle portion 504, a proximal portion 506, and a lumen extending therethrough.

Figure 6A:
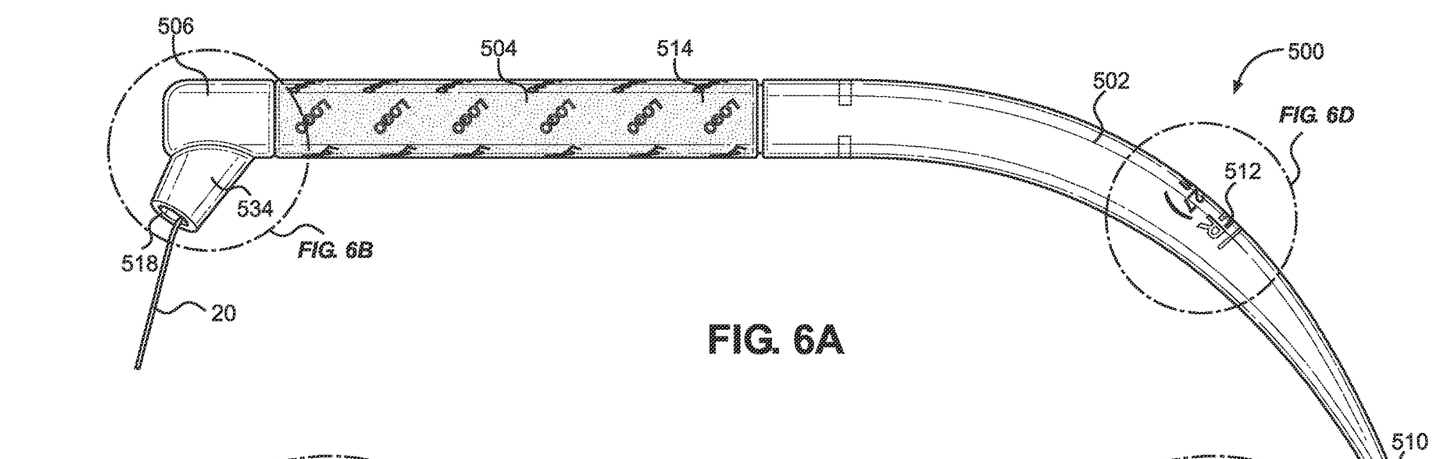
FIGS. 6A-6D illustrate a fifth exemplary embodiment of a tracheostomy dilator according to the present invention.
Figure 6B:
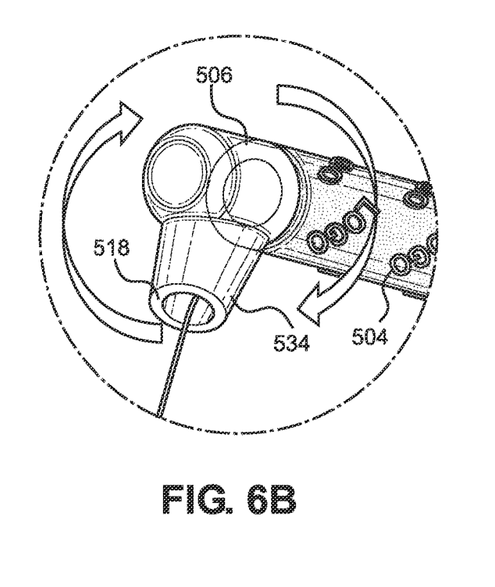
Figure 6C:
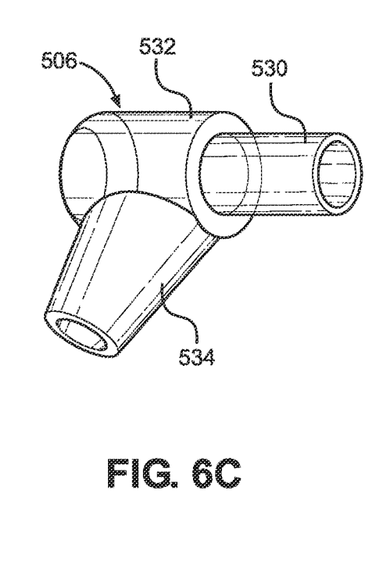
Figure 6D:
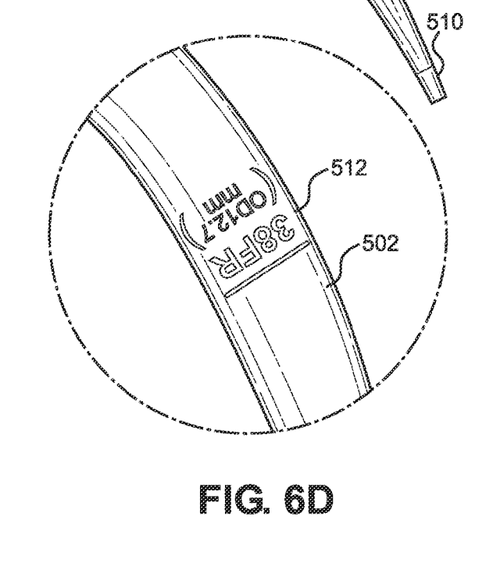

The distal portion 502 may including a continuous curve extending from the handle portion 504 to a distal tip 510 having a distal opening of the lumen. The continuous curve may enable the tracheostomy dilator 500 to pass through the trachea during insertion and for the distal tip 510 to clear the posterior tracheal wall. The distal portion 502 may taper along the continuous curve to the distal tip 510 to facilitate insertion. For example, the distal portion 502 may taper through a wall thickness that gradually reduces along the continuous curve to the distal tip 510. The distal portion 502 may have a hydrophilic coating to reduce friction during insertion into the tracheostomy, obviating the need for lubricating jelly. The distal portion 502 may also include indicia 512 of a size of a cross-section and a depth of the distal portion 502. For example, as illustrated in FIG. 6D, the indicia 512 may include a diameter (e.g., 38 French) and a line at least partially around the circumference indicating a proper depth for insertion of the distal portion 502 to dilate the tracheostomy.

The handle portion 504 may be substantially straight and include an elongated linear shaft integrally formed with the distal portion 502. The handle portion 504 may be proximal of the distal portion 502 and be configured to be grasped by a user. The handle portion 504 may be textured to increase grip and handling of the user. For example, the handle portion 504 may include a textured rubber sleeve 514 over the shaft. The grip on the textured surface may be enhanced by embossing a plurality of raised words and/or logos (e.g., of the manufacturer and/or distributor) along the length of the handle portion 504 and/or sleeve 514. The sleeve 514 may be received in an elongate recess on the outer surface of the shaft to prevent relative slipping.

The proximal portion 506 may be configured to deflect a guidewire 20 at an angle of least 30-45 degrees from a longitudinal axis of the handle portion 504. The proximal portion 506 may be detachable from the elongated linear shaft of the handle portion 504. For example, the proximal portion 506 may include a distal tubular extension 530 (as shown in FIG. 6C) that is frictionally received in the shaft of the handle portion 504. The distal tubular extension 530 may have a diameter less than a tubular portion 532 that extends uniformly from the handle portion 504. The proximal portion 506 may further include an angled off-axis extension 534 extending from the tubular portion 532 at an angle of at least 30-45 degrees relative to a longitudinal axis of the handle portion 504. The angled extension 534 may include a proximal opening 518 of the lumen, through which the deflected guidewire 20 passes out of the tracheostomy dilator 500 when advanced. As illustrated in FIG. 6B, the proximal portion 506 may be rotated about the longitudinal axis of the proximal portion 506 to position the angled extension 534 and proximal opening 518 in any radial direction. The rotation of the proximal portion 506 allows the reorientation of the guidewire 20, for example, depending on the desired grip of the user and/or whether the user is right-handed or left-handed. Thus, the proximal portion 506 may reduce or prevent pinching of the guidewire 20 when grasping the handle portion 504.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A tracheostomy dilator comprising:
   a distal portion having a curve extending to a distal opening and configured to dilate a tracheostomy tracheostoma;
   a handle portion proximal of the distal portion and configured to be grasped by a user;
   a lumen configured to receive a guidewire; and
   a proximal portion proximal of the handle portion and having a proximal opening in communication with the lumen, wherein the proximal portion is configured to deflect the guidewire at an angle of at least 30 degrees from a longitudinal axis of the handle portion,
   wherein the proximal portion has a bevel in a circumferential wall at the proximal opening, such that the circumferential wall extends further proximally at an upper portion than a lower portion.

2. The tracheostomy dilator of claim 1, wherein the angle is at least 45 degrees from the longitudinal axis of the handle portion.

3. The tracheostomy dilator of claim 1, wherein the handle portion is straight.

4. The tracheostomy dilator of claim 1, wherein the handle portion is textured.

5. The tracheostomy dilator of claim 4, wherein the handle portion includes a textured sleeve.

6. The tracheostomy dilator of claim 1, wherein the distal portion has a wall thickness that decreases along a length of the distal portion.

7. The tracheostomy dilator of claim 1, further comprising an indicator of a size of the tracheostomy dilator on the distal portion.

8. The tracheostomy dilator of claim 1, wherein the proximal portion is longitudinally aligned with the longitudinal axis of the handle portion.

9. The tracheostomy dilator of claim 1, wherein the bevel is curved.

10. The tracheostomy dilator of claim 1, wherein the proximal portion comprises a hole distal of the proximal opening and in communication with the proximal opening, and the hole is configured to receive the guidewire.

11. The tracheostomy dilator of claim 10, wherein the proximal portion comprises a slot connecting the proximal opening and the hole, and the slot has a width less than the proximal opening and the hole.

12. The tracheostomy dilator of claim 1, wherein the proximal portion is rotatable around the longitudinal axis relative to the handle portion.

13. The tracheostomy dilator of claim 1, wherein the proximal portion is detachable from the handle portion.

14. The tracheostomy dilator of claim 13, wherein the proximal portion includes an insert having a tubular segment received within the handle portion to detachably secure the proximal portion to the handle portion.

15. A tracheostomy dilator comprising:
    a distal portion having a curve extending to a distal opening and configured to dilate a tracheostomy;
    a handle portion proximal of the distal portion and configured to be grasped by a user;
    a lumen configured to receive a guidewire; and
    a proximal portion proximal of the handle portion and having a proximal opening in communication with the lumen, wherein the proximal portion is configured to deflect the guidewire at an angle of at least 30 degrees from a longitudinal axis of the handle portion, wherein the proximal opening is disposed at the angle from the longitudinal axis, and wherein the proximal portion has a bend from the longitudinal axis to the angle.

16. A tracheostomy dilator comprising:

a distal portion having a curve extending to a distal opening and configured to dilate a tracheostomy;

a handle portion proximal of the distal portion and configured to be grasped by a user;

a lumen configured to receive a guidewire; and a proximal portion proximal of the handle portion and having a proximal opening in communication with the lumen, wherein the proximal portion has a bevel, wherein the bevel is in a circumferential wall at the proximal opening, such that the circumferential wall extends further proximally at an upper portion than a lower portion.

17. The tracheostomy dilator of claim 16, wherein the proximal portion is longitudinally aligned with a longitudinal axis of the handle portion.

18. The tracheostomy dilator of claim 16, wherein the proximal portion comprises a hole distal of the proximal opening and in communication with the proximal opening, and the hole is configured to receive the guidewire, the proximal portion comprises a slot connecting the proximal opening and the hole, and the slot has a width less than the proximal opening and the hole.

* * * * *